United States Patent [19]

Kornguth et al.

[11] Patent Number: 5,230,883

[45] Date of Patent: Jul. 27, 1993

[54] METHOD FOR LOCALIZATION AND TREATMENT OF TUMORS USING POLYLYSINE COMPLEXES

[75] Inventors: Steven Kornguth; Patrick Turski; H. Ian Robins; Robert J. Nickles, all of Madison, Wis.

[73] Assignee: Wisconsin Alumni Research Foundation, Madison, Wis.

[21] Appl. No.: 825,884

[22] Filed: Jan. 27, 1992

Related U.S. Application Data

[63] Continuation-in-part of Ser. No. 518,362, May 3, 1990, abandoned, which is a continuation-in-part of Ser. No. 347,358, May 4, 1989, abandoned.

[51] Int. Cl.$^5$ ..................... G01N 24/08; A61K 37/00
[52] U.S. Cl. ......................... 424/9; 436/173; 436/806; 128/653.4; 514/12; 514/836; 424/1.1
[58] Field of Search ............ 424/9, 1.1; 436/173, 436/806; 128/653.4, 654; 514/836, 12

[56] References Cited

U.S. PATENT DOCUMENTS

| | | | |
|---|---|---|---|
| 4,331,647 | 5/1982 | Goldenberg | 424/1 |
| 4,352,751 | 10/1982 | Wieder et al. | 260/112 R |
| 4,639,365 | 1/1987 | Sherry | 424/9 |
| 4,675,173 | 6/1987 | Widder | 424/9 |
| 4,687,659 | 8/1987 | Quay | 424/9 |
| 4,728,575 | 3/1988 | Gamble et al. | 428/402.2 |
| 4,731,239 | 3/1988 | Gordon | 424/9 |
| 4,735,210 | 4/1988 | Goldenberg | 128/654 |
| 4,855,353 | 8/1989 | Kurami et al. | 525/54.1 |
| 4,863,717 | 9/1989 | Keana | 424/9 |
| 4,951,675 | 8/1990 | Groman et al. | 128/653.4 |
| 4,963,344 | 10/1990 | Gries et al. | 424/9 |
| 5,135,737 | 8/1992 | Keana | 424/9 |

FOREIGN PATENT DOCUMENTS 0331616 9/1989 European Pat. Off. .
1541436 2/1975 United Kingdom .

OTHER PUBLICATIONS

J. Neurosurg 66:898–906, 1987 "Magnetic Resonance Imaging of Gadolinium Labeled Monoclonal Antibody Polymers Directed at Human T Lymphocytes Implanted in Canine Brain", Kornguth et al.

S. Kornguth, "Preferential Binding of Radiolabeled Poly-L-lysine to C6 and U87 Glioblastomas Compared with Endothelia Cell in Vitro" Cancer Research 49:6390–5 (1989).

A. Rosowsky; "Regiospecific γ-Conjugation of Methotrexate to Poly (L-lysine)" Molecular Pharmacology 27:141–7 (1985).

*Primary Examiner*—Allen J. Robinson
*Assistant Examiner*—Gary E. Hollinden
*Attorney, Agent, or Firm*—Quarles & Brady

[57] ABSTRACT

Improved methods of selectively localizing, imaging and/or treating tumors, which have a net negative charge, employ novel compositions containing non-immunogenic complexes having a net positive charge in a sterile solution. The complexes contain polylysine, a linking agent bound to less than all of the lysyl groups of the polylysine, and an imaging agent or a chemotherapeutic agent which is also bound to the linking agent.

3 Claims, No Drawings

METHOD FOR LOCALIZATION AND TREATMENT OF TUMORS USING POLYLYSINE COMPLEXES

RELATED CASES

The present application is a continuation-in-part of our pending U.S. Pat. application No. 07/518,362 filed May 3, 1990, (now abandoned) which is a continuation-in-part of our U.S. Pat. application No. 07/347,358 filed May 4, 1989 (now abandoned).

FIELD OF THE INVENTION

The present invention relates to methods for the location and treatment of tumors and diagnostic compositions for use in such methods.

BACKGROUND OF THE INVENTION

The localization of tumors, such as astrocytomas in the brain in vivo and the determination of the margin between normal tissue and tumor can be useful for surgical, radiotherapeutic and chemotherapeutic approaches to the tumor. Although gliomas generally do not metastasize, they do recur locally after surgical resection and carry a grave prognosis (1). The grave prognosis results in part from the inability to delineate clearly the boundary between tumor and normal brain tissue, and from the restricted permeability of the blood brain barrier to imaging and therapeutic agents. The successful delivery of magnetic resonance contrast agents or of radionuclides for positron or gamma imaging might contribute to the more precise localization of tumor margins.

Monoclonal antibodies prepared against the tumor have been proposed for use in the past as effective carrier molecules for the delivery of contrast and radionuclide agents (2,3). However, the use of such monoclonal antibodies is accompanied by disadvantages. Antibodies are very large molecules that also can carry cross-reactive antigenic determinants that could cause problems. In addition, the monoclonal antibodies seldom bind more than 70% of cells, even in clonogenic tumors.

In addition to monoclonal antibodies, various synthetic polypeptides, such as polylysine which selectively binds to tumor cells as compared to normal brain cells, have been considered for use as carrier agents for therapeutic agents.

Notwithstanding prior efforts, a need still exists for reliable, safe methods for the localization, targeting and treatment of tumors and for complexes that can be used in such methods.

BRIEF SUMMARY OF THE INVENTION

The objects of the present invention include disclosing novel methods for the localization and the treatment of tumors.

The objects also include the disclosure of novel diagnostic compositions which can be used in such methods.

In the practice of the present invention, a safe and effective amount of a novel composition consisting essentially of non-immunogenic complex of a polylysine, a linking molecule and an imaging agent or a chemotherapeutic agent having a high net positive charge and a sterile liquid solvent for the complex is injected into the blood system of an animal. The complex is carried by the bloodstream to and selectively binds to tumors having a greater net negative charge than non-tumor cells. The method is especially useful for the imaging of polyanionic charged tumors such as Wilms tumors, brain tumors, small cell carcinoma of the lung and melanomas.

The novel complexes of the present invention comprise polylysine, a linking molecule and an imaging agent or a chemotherapeutic agent. In the complexes, the linking molecule is bound to less than about 30% of the lysyl residues of the polylysine so that the complexes have a high net positive charge and will bind selectively to tumors having a higher net negative charge than non-tumor cells. The preferred ratio of lysyl residues to linking agent will range from about 5 to 1 (20% of lysyl residues bound) to about 20 to 1 (5% lysyl residues bound).

The advantages of using complexes containing polylysine as the sole carrier vehicle are that: 1) polylysine is non-immunogenic which permits repetitive use as a carrier vehicle, 2) polylysine is a synthetic polymer and chemically homogeneous, 3) polylysine is available in different molecular sizes, 4) polylysine is easily modified to form complexes with tri- or tetravalent radionuclides, such as gadolinium and zirconium, 5) polylysine is easily labelled with iodide radionuclides using the Bolton Hunter reagent.

The ability to select polylysine polymers of low molecular weight can facilitate the delivery of the imaging or therapeutic agent through the areas where blood-brain barrier is intact without recourse to permeabilization with mannitol (2).

The ease with which polylysines may be modified with multiple nuclides provides an approach to determine dosage and concentration of polymer that is required for successful imaging in a patient population and for simultaneous imaging and therapy (e.g. with Gd and $^{90}Y$.)

The polylysine is not immunogenic as compared to immunoglobulins; therefore, the novel polylysine containing complexes are selective for any tumors having greater net negative charges than non-tumor cells and may be used for multiple imaging or multiple therapeutic procedures.

The primary advantage of immunoglobulins, such as antibodies, resides in the specificity of these proteins for particular tumors and in the relative lack of toxicity as compared with polylysine which exhibits toxicity at concentrations above 1.0 mg per 100 gm body weight (8,10,11). However, the unexpected sensitivity of the methods of the present invention permits the use of complexes containing polylysine concentrations that are not toxic.

Other objects and advantages of the present invention will be apparent from the description.

DESCRIPTION OF THE PREFERRED EMBODIMENT

In preparing the diagnostic composition of the present invention, the non-immunogenic complex is prepared by first covalently coupling the polylysine to a linking molecule, diethylene triamine pentaacetic acid dianhydride (DTPA), with a ratio of lysine residue/DTPA in the range of 5–20 lysyls per DTPA. This ratio assures that the complexes will have an adequate net positive charge to bind to tumors having a greater net negative charge than non-tumor cells.

The preferred degree of polymerization of the polylysine chain length is in the range of 50–100. The polylysine-DTPA complex is preferably separated from low molecular weight reagents by gel filtration chromatography on Sephadex G-25.

The imaging and chemotherapeutic agents, such as metal ions that are paramagnetic (e.g. gadolinium, manganese), positron emitters (e.g. 89Zr), gamma emitters (e.g. 153Gd) or beta emitters (e.g. 90Y), are then added to the polylysine-DTPA complex by citrate exchange and the low molecular weight materials present are separated from the polylysine-DTPA-metal ion complex by gel filtration. A paramagnetic component in the complex permits MR imaging, a positron emitter permits PET imaging and the presence of a beta emitter in the complex provides a radiotherapeutic agent.

The complexes are then dissolved in a liquid solvent, such as saline solution; packaged in containers and sterilized, if not already sterile, to provide a non-immunogenic diagnostic composition.

In the preferred practice of the methods of the present invention, a diagnostic composition of the present invention containing a selected complex is injected into the arterial system in the area of the suspected tumor so that the concentrations of polylysine are less than 100μg per 100 gms body weight. For example, excellent magnetic resonance images of C6 glioblastoma have been obtained with concentrations of about 0.35Mg per 100 grams of body weight. When the method is an imaging method, the MRI or PET imaging is then done in a conventional manner after a suitable time delay (24 to 96 hours) to permit maximum contrast between tumor and surrounding tissue.

Novel complexes of polylysine-DTPA and the metallic ions 153Gd and 89Zr have been found to bind to C6 astrocytoma and U87 MG glioblastoma cells six to eight times more readily than they bind to endothelial cells from the brain or the aorta and to provide superior imaging.

Many tumors have a greater net negative charge than non-tumor cells. Polylysine in the complexes contributes a positive charge that increases their tendency to bind to tumor cells. Therefore, the high net positive charge on the polylysine-DTPA-metal ion complexes, prepared as described, results in selective binding of the complex to the tumor cells.

The ingredients for preparing the novel compositions of the present invention may be provided in kit form for the convenience of users. In addition, the novel compositions of the present invention may also be supplied with other ingredients for use in test kits for the in vitro analysis of tumor cells, tumor cell fragments or tumor specific proteins in spinal fluid or plasma.

In the description that follows, the efficacy of compositions containing complexes of polylysine, DTPA and 153Gd, or 89Zr or 125I to image C6 astrocytoma in vivo in the rat brain are described.

Materials and Methods

Fluorescein-labelled polylysine hydrobromide (DP 88, weight average by light scattering), unmodified polylysine (DP 299 by light scattering, DP 267 by viscosity) and DTPA dianhydride were purchased from Sigma (St. Louis, MO). The 153Gd and the 125I Bolton-Hunter reagents (12) were purchased from DuPont-New England Nuclear (Boston, MA); the 89Zr was generated from an yttrium target by the reaction 89Y(P,n)89Zr in the 11 MeV proton beam of the University of Wisconsin, Medical Physics cyclotron (CTI, Inc.). The carrier free 89Zr was purified by the method of Scadden and Ballou (13). The 89Zr was coupled to the polylysyl DTPA on the day it was generated from the yttrium. At 24 hours after preparation, 1 picomole of carrier free 89Zr contains 300μg Ci.

The polylysine hydrobromide was dissolved in bicarbonate buffer (0.1 mol/1, pH 9.0); then, DTPA, dissolved in anhydrous dimethyl sulfoxide (DMSO), was added immediately to the polylysine. Polylysine-DTPA complexes were prepared with one DTPA per 16 lysyl residues. To prepare these complexes, a stoichiometric ratio of one DTPA dianhydride in DMSO was added per 10 lysyl residues. The reaction was permitted to proceed for 60 min. at 25° C.; then, the reactants were passed through G-25 Sephadex columns (PD-10 columns from Pharmacia, Piscataway, NJ) that were preequilibrated with citrate buffer (0.1 mol/1, pH 5.5). The polylysine-DTPA product emerged at the void volume of the column. In a similar manner, but with different stoichiometric ratios, polylysine-DTPA complexes containing other DTPA/lysine ratios were prepared.

The DTPA-modified polylysine in citrate buffer was reacted with gadolinium chloride (Aldrich Chem., Milwaukee, WI) dissolved in the same citrate buffer. The polylysine-DTPA-Gd chelates were then passed through G-25 Sephadex gel filtration columns, which were preequilibrated with 0.15 mol/1 of sodium chloride, to separate the free gadolinium from the polylysine-DTPA-Gd complex. The complexes containing zirconium and other metal ions can be prepared in a similar manner.

The C6 astrocytoma cells were cultured in Ham's F-10 medium, supplemented with 2.5% fetal calf serum (Hyclone Lab, Logan UT), 15% horse serum (Gibco), 100μg streptomycin and 100 units penicillin per ml, and 1.2 gm bicarbonate buffer per liter.

Male Wistar Furth rats (over 300 gms each) were purchased from Harlan Sprague Dawley (Indianapolis, IN). The rats were anesthetized with chloral hydrate and a 0.5 mm burr hole was placed over the left frontal cortex of each rat 3 mm to the left of the midline. Each of 6 rats was then injected with $2 \times 10^6$ C6 astrocytoma cells in 10μg of F-10 Ham's medium containing 0.5% agarose (Sigma). Two other rats were injected with the same medium, but without tumor cells. Eight days later the rats were anesthetized with chloral hydrate and the brains were imaged by MRI to visualize the tumor cell injection site. The animals were catheterized through the femoral artery to the ascending aorta. Then sterile compositions containing 500 ul of saline solution containing 100 ug of 125I polylysine (Bolton Hunter), or 100 ug of 153Gd-and 157Gd-labelled polylysine or 100 ug of 89Zr labelled polylysine were prepared and injected into the aorta. Each rat received 0.23 mCi 89Zr. The animals were permitted to recover for three additional days to permit the background radiation level to fall. On the 11th day after tumor implantation the animals were anestheized with chloral hydrate and imaged by the Signa MRI using the GE extremity coil (17 cm diameter). The T1 weighted images were obtained at either 3 or 4 mm thickness (TR=600; TE=20).

Blood samples were taken from the rats while they were under anesthesia and the samples were retained for analysis of radionuclides; the rats were sacrificed by exsanguination, placed in the PET imager in groups of four and counted for 14 hours. The PET images were generated by a CTI Inc Model 933/04-12. It provides a 4 ring, 7 slice positron tomograph with 5 mm full width, half maximum (FWHM) spatial resolution (transverse) and 6 mm FWHM resolution axially.

The brains and kidneys of each animal were removed after imaging. The liver, lungs, spleen, thyroid, testes, bone, heart and pancreas of animal three (a tumor recipient) were removed. All three nuclides were measured in the tissue samples by analysis with a Ge(Li)-type counter (15% efficiency germanium gamma spectrometer).

Tissue histology was performed on all brain samples to validate the location of the implanted C6 cells. Frozen sections (10 um) of formalin fixed brains were cut, stained with thionine and covered with DePex embedding material (Gurr Microscopy Ltd) and a cover slip. The sections were examined in a Leitz-DADS microscope and photographed.

Results

Poly-L-lysine hydrobromide (DP88) was modified covalently with either the chelator, DTPA or with 125I-Bolton Hunter reagent. The polylysine-DTPA was then reacted either with the positron emitter 89Zr, or paramagnetic stable gadolinium and the gamma emitter 153Gd. The 89Zr was produced in the 11 meV cyclotron by the reaction 89Y(p,n)89Zr and purified by fractional solubilization techniques utilizing acid and organic solvents. The polylysine-DTPA-nuclide and the polylysine-iodide complexes were separated from the unbound nuclide or metal ion by gel chromatography. Wistar Furth rats were implanted intracranially with C6 astrocytoma and 8 days later they were injected, through a catheter placed in the aorta, with the polylysine nuclide complexes. On the eleventh day after tumor implantation the rats were imaged by magnetic resonance imaging (MRI), and by positron emission tomography (PET). The organs were removed from the rats and the amount of each nuclide was determined by Ge(Li) counting. Frozen sections of the brains were prepared and stained with thionine to validate the tumor growth and the margin between tumor and normal brain. The signal intensity (SI) of the T1 weighted MR images revealed enhancement by the polylysine-DTPA-Gd; the central region of the tumor had a low SI with a high SI at the periphery in all cases. Ge(Li) counting revealed a 3-8 fold higher level of 89Zr in the tumor containing hemisphere than in the non-tumor hemisphere in 4 of 5 rats surviving 11 days with the implanted tumor. The PET revealed the whole body distribution of the polylysine-DTPA-89Zr; the major organs labelled were the tumor, kidney, spleen, thymus, heart, bone, testes and liver and the radioactivity recorded on a counts per second per gram normalized basis. Cytological studies of the thionine stained sections revealed good correlation with the tumor morphology as demonstrated by MR imaging. These observations suggest that polylysine-DTPA-Gd and polylysine-DTPA-89Zr complexes may have utility in detecting the margin between astrocytoma and normal brain by MRI and possibly by PET. Polylysine-DTPA-beta emitting metal nuclide complexes may have utility in radiotherapy of such tumors in situ.

In the description that follows, the magnetic resonance images of the brains of the rats injected with the C6 astrocytoma will be described first. The MR images obtained pre- and post-injection of the modified polylysine will be discussed. The MR images obtained from tumor free rats that were injected with the modified polylysines will also be discussed. Then the positron emission tomographs obtained from the rats will be discussed. The distribution of the polylysine-DTPA-nuclides derivatives in the brain and other organs, as determined by Ge(Li) counting, will then be described. Finally the histology of the tumor in situ will be discussed.

Magnetic Resonance Imaging of the Rat Brain implantation. The images of the 3 tumor bearing rats were similar. These images were obtained prior to injection of the gadolinium, zirconium and iodide labeled polylysines (DP88). It may be observed that some degree of asymmetry is detectable at this stage (animal 2 and animal 3) and one animal had a low signal intensity (SI) on T1 weighted images (TWI) in the region of the implanted tumor (animal 6). The control animals injected with cell free agarose, by contrast, revealed no unusual features at the same plane of section (animal 8). The images were taken at three mm thickness.

On the 11th day after tumor implantation and the third day after injection of the radionuclide-labelled polylysines (DP88), a circular central region of low signal intensity (SI) on the T1 weighted images (TWI), and a circumference of high SI in the same region of animal 2 was observed. The peripherally increased SI is also seen in the adjacent 3 mm MRI image from this animal. The MRI of animal 3 also shows low central SI on T1 and high SI in the circumference. The tumor containing region of animal 6 also reveals a low SI on TWI in the central region and a high SI in the circumference. The right hemisphere however, also has a large central region of law SI. The latter point is relevant since the organ counts of the 89Zr-DTPA-polylysine reported below for rat 6 indicate a higher distribution of the polylysine-DTPA-89Zr in the right hemisphere than in the left. A similar study of control rat brain (animal 8) revealed no areas of tumor-like appearance. Of the 6 rats that were injected with tumors, 5 survived to day 11 after tumor implantation; all 5 had tumor growth identified and the MRI of these brains revealed the tumor location and morphology. The high SI and TWI at the tumor margin is consistent with an enhancement of the relaxation of water protons caused by the localization of the Gd-DTPA polylysine complex in the tumor. The central zone of the C6 astrocytoma in the rat brain is frequently necrotic, an observation consistent with the low SI images obtained. The tumor region is clearly resolved in the 3 mm thick sections when the extremity coil is used. The tumor histology section below indicates that there was no evidence of hemorrhage in the tumor area or surrounding brain.

PET of the Tumor Containing and Control Rats

The positron emission tomographs of the rats were obtained in 7 planes, from the dorsal to the ventral surface of the rats. Four rats were imaged simultaneously and ring sources were used to correct for position in the apparatus. Each set of animals was imaged for 10 hours or longer to obtain the data for image reconstruction. These images reveal that the majority of the 89Zr-DTPA-polylysine was localized in the kidneys and a second major area of positron source was the snout. It was of interest in this regard that the animals, all of whom received 300 ug of polylysine, had blood in the urine and 2 evidenced nose bleeds. Further examination of the tomographs indicated that the brain does contain substantial positron emission activity. The localization of the Zr source to the right or left hemisphere by PET is difficult to ascertain. The apparent advantage of the PET over MRI is a rapid evaluation of the distribution of the Zr source in the whole body and the low concentration of polylysine required for imaging. The MRI clearly resolves the tumor area and permits demarcation of the tumor zone from the normal brain.

Organ Distribution of the Nuclide Labelled Polylysine

The brain was separated into the right and left hemisphere for determination of the counts per second of each nuclide in the organ. The tumor cells in all cases were implanted in the left frontal region of the brain. Table I below reports the counts per sec per gram tissue normalized to the whole rat body for each animal. The nuclide distribution was determined with a Ge(Li) counter; the 89Zr was measured from the 909 keV peak, the 153Gd from the 105 keV peak and the 125I from the 27keV peak. An aliquot of the injected polylysine nuclide material was used for calculating the organ distribution of the radionuclides.

From Table I, it may be observed that the distribution of the Zr was three to eight times higher in the left hemisphere (containing the tumor) than in the right in four of the 5 surviving rats that were injected with tumors. In one rat that contained C6 tumor, the right hemisphere had more radioactivity. The gadolinium reflected a similar increased localization in the left hemisphere but the proportion of the left in the compared with the right hemisphere was smaller than that observed for the Zr. There is some disproportionation of the Gd and Zr distribution even though both were chelated with the DTPA on polylysines of identical polymer size. This suggests that either the DTPA-Gd is released at a different rate from the polylysine chain than the DTPA-Zr or that the polylysyl-DTPA-Gd metabolite of polylysine localizes differently from lysyl-DTPA-89Zr. Because the polylysyl-DTPA-Gd complex contained more metal ion (cold Gd was added) than the Zr complex, it is possible that the excess metal in the Gd-DTPA complex affected nuclide distribution. The iodide label was equivalent in both hemispheres. This is consistent with the recognized loss of iodide from iodide labeled proteins in the presence of serum and other tissue fluids. The Zr is the label of choice from these observations and the iodide is least preferred of the three nuclides.

TABLE I

Distribution of each of three Polylysine-DTPA-Nuclide Derivatives in the Left and Right Brain Hemispheres

| | 89Zr | | 153Gd | | 125I | |
|---|---|---|---|---|---|---|
| Rat | Left | Right | Left | Right | Left | Right |
| 2 | 0.212 | 0.063 | 0.030 | 0.021 | 0.004 | 0.004 |
| 3 | 0.851 | 0.108 | 0.051 | 0.034 | 0.008 | 0.006 |
| 4 | 0.300 | 0.087 | 0.038 | 0.020 | 0.007 | 0.003 |
| 5 | 0.365 | 0.057 | 0.060 | 0.031 | 0.007 | 0.009 |
| 6 | 0.713 | 1.521 | 0.031 | 0.262 | 0.005 | 0.006 |
| 7 | 0.075 | 0.062 | 0.047 | 0.054 | 0.006 | 0.007 |
| 8 | 0.078 | 0.068 | 0.063 | 0.027 | 0.015 | 0.010 |

The distribution of the nuclides in other organs of the body is illustrated in Table II using rat 3 as an example. This table reveals that the organs with highest Zr contents are the kidney, spleen, heart, thymus, bone and testes. The high nuclide content of the spleen, heart, thymus and testes is anticipated since the polylysine was injected directly into the aorta. Positron emission tomographs of the rats reflect the Ge(Li) counts as anticipated and the PET may be used to follow temporally the polylysine-DTPA-89Zr organ distribution. When normalized to kidney, the ratio of the Zr to the Gd differs in several organs indicating that Zr uptake is high in bone and low in liver whereas Gd is high in liver.

TABLE II

Distribution of Polylysine-DTPA-Nuclide in Organs of Rat 3 Counts per Sec per gm tissue normalized to the whole body

| | 89Zr | 153Gd | 125I |
|---|---|---|---|
| Kidney | 12.472 | 1.739 | 1.276 |
| bone | 2.500 | 0.323 | 0.004 |
| heart | 3.208 | 0.950 | 0.016 |
| liver | 0.922 | 2.844 | 0.092 |
| lung | 1.414 | 0.243 | 0.005 |
| testes | 2.604 | 0.040 | 0.000 |
| thymus | 3.055 | 0.617 | 0.012 |
| spleen | 5.520 | 9.193 | 1.351 |
| pancreas | 1.427 | 0.678 | 0.027 |

Histology of the C6 Astrocytoma in the Brain

The thionine stained sections of the formalin fixed rat brains clearly revealed nests of tumor cells. The tumor cells were located at discrete sites in the left hemisphere, including the frontal and the parietal cortex. The tumors in the brain, that were revealed by histological stain, correlated with the sites revealed by MRI. From the histological examination it may be seen that the tumor infiltrated the normal brain tissue around the tumor. The tumor proper contains small round cells and larger round cells with pale nuclei and condensed chromatin. The histology confirms that the C6 tumors grew in the adult Wistar Furth rats, that the cell type and structure is consistent with the properties of the C6 tumor line, and that the MRI images obtained in vivo correlate with the histological appearance of the tissue. There was no evidence of hemorrhagic changes in the tumor or surrounding brain even though necrotic central zone could be seen in some tumors.

From the foregoing it is clear that diagnostic, non-immunogenic compositions containing polylysine DTPA and a paramagnetic ion, such as Gd, enhance the MRI of intracerebral tumors. The distribution of the polylysine-DTPA-89Zr, as determined by Ge(Li) counting, is higher in the tumor containing hemisphere by a factor of 3–8, than in the contralateral side. These data represent the first successful use of a tumor selective carrier vehicle, polylysine, to deliver paramagnetic Gd and positron emitting 89Zr in vivo to a syngenic model rat glioma for the purposes of neuroradiological imaging. This delivery system enhanced the relaxation of water in the area of the C6 astrocytoma. The proof of principle that polylysine-DTPA-89Zr may be used for the PET imaging of intracranial tumors has also been demonstrated. These results are consistent with an earlier study from our laboratories which indicated that C6 astrocytoma cells and U87 MG glioblastoma cells, in vitro, bind 6–8 fold times more polylysine-DTPA-89Zr than does endothelial cells from brain or aorta.

Other investigators have previously imaged C6 tumors by MR, in vivo, with the use of a 10 Cm internal diameter coil (17). Rats with intracerebral C6 tumors were injected with DTPA-Gd (17) and their brains were imaged. The DTPA-Gd treatment enhanced the relaxation of water protons and provided MRI contrast. DTPA-Gd penetrates the tumor region in the brain transiently, as a result of a compromised blood brain barrier. The influx of the DTPA-Gd and efflux is relatively rapid because the DTPA is not bound by the tumor. The advantage of the polylysine-DTPA-Gd complex compared with DTPA-Gd alone resides in the selective binding of the polylysine to the tumor cell surface. Because the polylysine is bound by the tumor, the imaging may be performed after the blood level of the contrast material (i.e. polylysine) has fallen to very low levels. The signal to noise ratio is thus enhanced by the use of polylysine.

The polylysine can also be used to deliver several nuclides or chemotherapeutic agents simultaneously, because of the abundance of epsilon amino groups on the polymer. This permits an analysis of drug delivery or of radiation dosage effects by a comparison of the PET image with the MRI image. Polylysine does exhibit toxic properties at concentrations exceeding 1.5 mg per 100 gm body weight in the rat (10,11). However the picomole concentrations of 89Zr, Gd and 90Y required for PET imaging, for MRI or for radiotherapy is several magnitudes below toxic concentrations. Polylysine has been used a complexing agent for poly I:poly C in the chemotherapy of tumors (18), and for the delivery of methotrexate to ovarian cells (19). The toxicity problem is therefore amenable to solution.

The C6 astrocytoma is a good model for human gliomas because the tumor produces S-100 (20), glutathione S transferase (21) and glial maturation factor (22). The successful imaging of this tumor in vivo has direct applications to the imaging of human brain gliomas in vivo. In the human subject the polylysine-DTPA-nuclide complex will have greater utility than in the rat. The placement of the catheter into the carotid artery in the area of the tumor is readily achieved as is discernment by PET of the tumor mass. The size of the rat brain (0.8–1.0 cm dorsal ventral dimension) approximates that of a single PET slice (5 mm). This resolution in a human brain provides the information necessary to determine the tumor margin and the suitability of surgery.

The polylysine polymers preferred for use in the complexes of the compositions of the present invention are those lysine polypeptide or homopolymers having a molecular weight of about 5,000 to about 20,000 dalton. They can be made by the process described in U.S. Pat. No. 3,215,684. Any polylysine which covalently bonds to the chelating agent and possesses an adequate net positive charge to be attracted to and bind to tumor cells and a favorable toxicity ratio can be used.

The preferred chelating agent for use in the complexes is DTPA which is also known as pentetic acid and diethylenetriamine pentaacetic acid. The purpose of the chelating agent is to covalently bind to the polylysine and the metallic ions which are imaging or therapeutic agents. DTPA can be prepared as described in U.S. Pat. No. 2,384,816. Other chelating agents that might be used include ethylene diamine tetraacetic acid and DOTA.

Representative of metallic agents that can be used as MR imaging agents in the complexes are paramagnetic ions such as gadolinium, manganese, and cobalt.

Representative of the metallic ions which can be used as PET imaging agents are 89Zr, and 152Mn or 55Co.

Representative of the ions that can be used as q-camera imaging agents is 111In.

Representative of metallic ions that can be used as therapeutic agents in the complexes are 90Y and 211A+(astatine).

Two other technologies that have clinical utility in tumor studies are possible because of the binding of polylysine containing complexes or probes to tumor cells: a) Spinal fluid samples may be centrifuged at low speed, 1000g for 10 minutes, to recover any cell or cell fragments present. Spinal fluid normally does not contain cells but may contain cells or cell fragments in the case of central nervous system tumors. The resultant pellet is resuspended in bicarbonate buffer containing saline and the radiolabelled polylysine is added to the suspension. The cell suspension is recentrifuged at the same force indicated above, the pellet recovered and washed three times with the buffer. The pellet is then counted to determine the number of cells per volume of spinal fluid. b) Spinal fluid samples or samples of blood plasma can be incubated with polylysine probes (polylysine alone, polylysine-DTPA-metal ions, polylysine-fluorescein [or other fluorescent probe]). The mixture is centrifuged at low speed, <2000g, for 10 minutes. The pellets are resuspended in bicarbonate buffer and applied to pure nitrocellulose membranes.

The polylysine probes bind avidly to the nitrocellulose membrane, even when the polylysine is complexed with other materials. The tumor cell-polylysine complexes also will adhere to the membrane. The cells on the membrane may then be incubated with immunoglobulins that are specific for particular tumor cell types. These immunoglobulins are available commercially or can be prepared. Then traditional western blot procedures can be employed to yield spot tests which identify the tumor cell fragments adherent to the nitrocellulose membrane. Specifically, the initial anti-tumor immunoglobulin may be of varied origin, i.e. from the patient, mice, sheep, goat etc. Depending upon the source of the initial immunoglobulin, a second immunoglobulin (i.e. anti-human, anti-mouse, anti-sheep, anti-goat IgG and IgM) coupled to a reporter molecule such as peroxidase or phosphatase, is incubated with the nitrocellulose membrane. The membranes are washed after each step. Finally the membranes are incubated with an appropriate substrate which yields a new signal (e.g. color, electric output).

The compositions of the present invention for use as diagnostic agents or therapeutic agents are comprised of one of the described non-immunogenic complexes dissolved in a sterile liquid solvent, such as saline solution and Sterile Water for Injection U.S.P., and packaged as a sterile preparation in a sealed container, such as a vial or ampule. The exact composition and concentration of the complex in the composition will depend upon its intended use. However, in general the concentration of ingredients will be such that the injection of the entire contents will result in a less than toxic dose, which for polylysine is about 1.5mg per 100 gms of body weight. The preferred route of administration is intra-arterially at a site near the site of the suspected tumors.

It will be apparent to those skilled in the art that a number of modifications and changes may be made without departing from the spirit and scope of the present invention. Therefore, it is intended that scope of invention not be limited by the foregoing specific description but only by the claims.

REFERENCES

1. Lyons BE, Strohbehn JW, Roberts DW, Wong TZ and Britt RH. Interstitial microwave hyperthermia for the treatment of brain tumors. In: Hyperthermia in Cancer Treatment, eds Anghileri LJ and Robert J. CRC Press Inc., Vol. 3, pp 25–46, 1986.

2. Kornguth SE, Turski PA, Perman WH, Schultz R, Kalinke T, Reale R and Raybaud F. Magnetic Resonance Imaging of Gadolinium-labeled Monoclonal Antibody Polymers Directed at Human T Lymphocytes Implanted in Canine Brain J Neurosurg 66:898–906, 1987.

3. Wakabayashi T, Yoshida J, Seo H, Kazo K, Murata Y, Matsui N, Kageyama N Characterization of Neuroectodermal Antigen by a Monoclonal Antibody and its Application in the CSF Diagnosis of Human Glioma. J Neurosurg 68: 449–455, 1988.

4. EJ Ambrose DM Easty PCT Jones, Specific Reactions of Polyelectrolytes with the Surfaces of Normal and Tumor Cells. Brit J Cancer 12: 439–447, 1958.

5. Kornguth S and Stahmann M. Effect of Polylysine on the Leakage and Retention of Compounds by Ehrlich Ascites Tumor Cells. Canc Res 21: 907–912, 1961.

6. Kornguth S, Stahmann M and Anderson J. Effect of Polylysine on the Cytology of Ehrlich Ascites Tumor Cells. Exptl Cell Res 24: 484–494, 1961.

7. Richardson T, Hodgett J, Lindner A, Stahmann M, Action of Polylysine on Some Ascites Tumors in Mice. Proc. Soc Exptl Biol Med 101, 382–386, 1959.

8. Sela M, Katchalski E, Biological Properties of Poly alpha Amino Acids. Adv in Protein Chemistry 14, 391–478, 1959.

9. Gu JM, Robinson J, Leung S. Binding of Acrylic Polymers to Mucin Epithelial Surfaces: Structure Property Relationships, CRC Critical Reviews in Therapeutic Drug Carrier Systems 5:21–67, 1958.

10. de Vries A, Feldman JD, Stein O, Stein Y, Katchalski E. Effects of Intravenously Administered Poly DL-lysine. Proc Soc Exptl ,Biol Med 82: 237–240, 1953.

11. Rubini JR, Stahmann MA, Rasmussen AF. Agglutination of Red Cells by Synthetic Lysine Polypeptides Proc Soc Exptl Biol Med 76: 659–662, 1951.

11. Rubini JR, Stahann MA, Rasmussen AF. Agglutination of Red Cells by Synthetic Lysine Polypeptides Proc Soc Exptl Biol Med 76: 659–662, 1951.

12. Bolton AE, Hunter W, The Labelling of Proteins to High Specific Radioactivities by Conjugation to a 125I-Containing Acylating Agent. Biochem J 133:529-1973.

13. Scadden EE, Ballou NE. Solvent Separations of Zirconium and Niobium. Anal Chem 25: 1602–1604, 1953.

14. Krejcarek G and Tucker K. Covalent Attachment of Chelating Groups To Macromolecules Biochem Biophys Res Commun 77:581–585, 1977.

15. Hnatowich DJ, Layne WW, Childs RL et. al. Radioactive Labeling of Antibody: A Simple and Efficient Method Science 220: 613–615, 1983.

16. Paik CH, Murphy PR, Eckelman WC et. al. Optimization of the DTPA Mixed Anhydride Reaction with Antibodies at Low Concentration. J Nucl Med 24: 932–936, 1983.

17. Runge VM, Jacobson S, Wood M, Kaufman D, Adelman L, MR Imaging of Rat Brain Glioma:Gd-DTPA versus Gd-DOTA. Radiology 166: 835–838, 1988.

18. Lampkin BC, Levine AS, Levy H, Krivit W, Hammond D, Phase II Trial of a Complex Polyriboinosinic-Polyribocytidilic Acid with Poly-L-lysine and Carboxy Methyl Cellulose in the Treatment of Children with Acute Leukemia and Neuroblastoma. Cancer Res 45: 5904–5909, 1985.

19. Ryser H J-P, Mandel R, Hakobian A, Shen W, Methotrexate-Poly(lysine) as a Selective Agent for Mutants of Chinese Hamster Ovary Cells Defective in Endocytosis. J. Cell. Physiol. 135: 277–284, 1988.

20. van Eldik, LJ and Zimmer DB, Secretion of S-100 from Rat C6 Glioma Cells. Brain Res 436: 367–370, 1987.

21. Senjo M and Ishibashi T Possible Involvement of Glutathione S. Transferases in the Cell Growth of C6 Astroglioma Cells. J Neurochem 50: 163–166, 1988.

22. Lim R, Hicklin DJ, Ryken TC, Miller JF, Endogenous immunoreactive Glia Maturation Factor-like Molecules in Astrocytes and Glioma Cells. Brain Res 430: 49–57 1987.

The embodiments of the invention in which an exclusive property or privilege is claimed are the following:

1. A method for the diagnostic imaging of a tumor having a high net negative charge in a human which comprises bringing into binding contact with said tumor in said human a diagnostically effective amount of a complex having a high net positive charge, said complex comprising polylysine, a linking agent bonded to less than about thirty percent of the lysyl groups of said polylysine and an imaging agent bonded to the linking agent.

2. A method of selectively imaging with MR a tumor having a high net negative charge in an animal which comprises first administering to an animal having a tumor or suspected or having a tumor a diagnostically effective amount of a complex having a positive net charge and comprising polylysine having a linking agent bonded to less than about thirty percent of the lysyl groups thereof, said linking agent also being bound to an MR imaging agent; and, then subjecting the animal to MR imaging.

3. A method of delivering an MR imaging agent to a tumor having a net negative charge in an animal, said method comprising introducing into the bloodstream of an animal having such a tumor a diagnostically effective amount, a non-immunogenic complex having a net positive charge, said complex and comprising polylysine having covalently bonded to less than thirty percent of the lysyl groups thereof, a linking agent which also is attached to an MR imaging agent; and allowing the complex to be attracted to the tumor.

* * * * *